(12) United States Patent
Kumar et al.

(10) Patent No.: US 8,101,630 B2
(45) Date of Patent: Jan. 24, 2012

(54) EXTENDED RELEASE OPIOID ABUSE DETERRENT COMPOSITIONS AND METHODS OF MAKING SAME

(75) Inventors: Vijai Kumar, Morris Plains, NJ (US); David Dixon, Woodside, NY (US); Divya Tewari, Suffern, NY (US); Dilip B. Wadgaonkar, Suffern, NY (US)

(73) Assignee: Acura Pharmaceuticals, Inc., Palantine, IL (US)

( * ) Notice: Subject to any disclaimer, the term of this patent is extended or adjusted under 35 U.S.C. 154(b) by 255 days.

(21) Appl. No.: 12/383,906

(22) Filed: Mar. 30, 2009

(65) Prior Publication Data

US 2009/0253730 A1 Oct. 8, 2009
US 2010/0216829 A2 Aug. 26, 2010

Related U.S. Application Data

(63) Continuation of application No. 10/723,654, filed on Nov. 26, 2003, now Pat. No. 7,201,920, and a continuation of application No. 11/716,122, filed on Mar. 9, 2007, now Pat. No. 7,510,726.

(51) Int. Cl.
*A61K 31/44* (2006.01)
*A61K 9/00* (2006.01)
*A61K 9/22* (2006.01)
*A61K 9/24* (2006.01)
*A61K 9/52* (2006.01)

(52) U.S. Cl. ........ 514/282; 424/400; 424/457; 424/484; 424/486

(58) Field of Classification Search ................. 514/282; 424/400, 457, 484, 486
See application file for complete search history.

(56) References Cited

U.S. PATENT DOCUMENTS

| | | | | |
|---|---|---|---|---|
| 6,524,618 | B1 * | 2/2003 | Kumar et al. | 424/468 |
| 6,572,885 | B2 * | 6/2003 | Oshlack et al. | 424/456 |
| 7,201,920 | B2 * | 4/2007 | Kumar et al. | 424/454 |
| 7,510,726 | B2 * | 3/2009 | Kumar et al. | 424/454 |
| 2009/0142378 | A1 * | 6/2009 | Frisbee | 424/400 |

* cited by examiner

*Primary Examiner* — James H. Alstrum-Acevedo
(74) *Attorney, Agent, or Firm* — Morgan, Lewis & Bockius LLP

(57) ABSTRACT

This invention relates to an abuse deterrent dosage form of opioid analgesics, wherein an analgesically effective amount of opioid analgesic is combined with a polymer to form a matrix.

1 Claim, 7 Drawing Sheets

EXTENDED RELEASE OPIOID ABUSE DETERRENT COMPOSITIONS AND METHODS OF MAKING SAME

STATEMENT OF RELATED APPLICATIONS

This application is a continuation of U.S. patent application Ser. No. 10/723,654, filed on Nov. 26, 2003 now U.S. Pat. No. 7,201,920; and Ser. No. 11/716,122, filed on Mar. 9, 2007 now U.S. Pat. No. 7,510,726, the entire contents of which are hereby incorporated by reference.

FIELD OF INVENTION

This invention pertains to abuse deterrent compositions containing a drug (e.g., an analgesic opioid). Additionally, the invention relates to a method of administering a dose of an analgesic from a dosage form, which is abuse deterrent.

BACKGROUND OF THE INVENTION

The class of drugs exhibiting opium or morphine-like properties are referred to as opioids, or opioid agonists. Certain opioids act as agonists, interacting with stereo specific and saturable binding sites in the brain and other tissues. Endogenous opioid-like peptides are present in areas of the central nervous system that are presumed to be related to the perception of pain; to movement, mood and behavior, and to the regulation of neuroendocrinological functions. Three classical opioid receptor types, mu ($\mu$), delta ($\delta$), and kappa ($\kappa$), have been studied extensively. Each of these receptors has a unique anatomical distribution in the brain, spinal cord, and the periphery. Most of the clinically used opioids are relatively selective for $\mu$ receptors, reflecting their similarity to morphine. However, it is important to note that opioid containing drugs that are relatively selective at standard doses will often interact with additional receptor subtypes when given at sufficiently high doses, leading to possible changes in their pharmacological effect. This is especially true as opioid doses are escalated to overcome tolerance.

The potential for the development of tolerance, physical and/or psychological, dependence (i.e., addiction) with repeated opioid use is a characteristic feature of most opioid containing drugs. The possibility of developing addiction is one of the major concerns in the use of opioids for the management of pain. Another major concern associated with the use of opioids is the diversion of these drugs from a patient in legitimate pain to other individuals (non-patients) for recreational purposes.

Drug abusers and/or addicts typically may take a dosage form containing one or more opioid analgesics and crush, shear, grind, chew, dissolve and/or heat, extract or otherwise damage the product so that a significant amount or even an entire amount of the drug becomes available for immediate absorption by 1) injection, 2) inhalation, and/or 3) oral consumption.

There are three basic patterns of behavior leading to opioid abuse. The first involves individuals whose opioid drug use begins in the context of medical treatment and who obtain their initial drug supplies through prescriptions from physicians. The second begins with experimental or "recreational" drug use and progresses to more intensive use. A third pattern of abuse involves users who begin in one or another of the preceding ways but later switch to oral opioids such as methadone, obtained from organized addiction treatment programs.

There are various routes of administration an abuser may commonly attempt to abuse an opioid containing drug formulation. The most common methods include 1) parenteral (e.g. intravenous injection), 2) intranasal (e.g., snorting), and 3) repeated oral ingestion of excessive quantities of orally administered tablets or capsules. One mode of abuse of oral solid drugs involves the extraction of the opioid component from the dosage form by first mixing the dosage form with a suitable solvent (e.g., water), and then subsequently extracting the opioid component from the mixture for use in a solution suitable for intravenous injection of the opioid to achieve a "high."

Attempts have been made to diminish abuse of orally administered opioid drugs. These attempts generally centered on the inclusion in the oral dosage form of an opioid antagonist which is not orally active but which will substantially block the analgesic effects of the opioid if one attempts to dissolve the opioid and administer it parenterally.

For example, commercially available Talwin®Nx tablets from Sanofi-Winthrop contain a combination of pentazocine and naloxone. Pentazocine is a partial agonist of $\mu$ receptors and also has affinity for $\kappa$ receptors, whereas, naloxone is an antagonist of $\mu$ receptors. Talwin®Nx contains pentazocine hydrochloride equivalent to 50 mg base and naloxone hydrochloride equivalent to 0.5 mg base. Talwin®Nx is indicated for the relief of moderate to severe pain. The amount of naloxone present in this combination has no action when taken orally, and will not interfere with the pharmacologic action of pentazocine. However, this amount of naloxone given by injection has profound antagonistic action to opioid analgesics. Thus, the inclusion of naloxone is intended to curb a form of misuse of oral pentazocine, which occurs when the dosage form is solubilized and injected. Therefore, this dosage has lower potential for parenteral misuse than previous oral pentazocine formulations.

U.S. Pat. No. 6,559,159 (Carroll et al.) describes the use of kappa receptors antagonist for the treatment of opioid related addictions. One such compound is naltrexone, which is commercially available in the tablet form Revia® for the treatment of alcohol dependence and for the blockade of exogenously administered opioids. (Physicians Desk Reference 57th ed., Montvale, N.J.)

U.S. Pat. No. 6,375,957 (Kaiko et al.) describes in detail the combination of opioid agonist, NSAID, and an orally active opioid antagonist. The purpose of adding the opioid antagonist is the same as discussed above.

U.S. Pat. No. 4,457,933 (Gordon et al.) describes in detail a method for decreasing both the oral and parenteral abuse potential of analgesic agents such as oxycodone, propoxyphene and pentazocine by combining an analgesic dose of the analgesic agents with naloxone in specific, relatively narrow ranges.

U.S. Pat. No. 6,228,863 B1 (Palermo et al.) describes a method for reducing the abuse potential of an oral dosage form of an opioid analgesic, whereby an orally active opioid agonist is combined with an opioid antagonist into an oral dosage form requiring at least a two-step extraction process to be separated from the opioid agonist, the amount of opioid antagonist included being sufficient to counteract opioid effects if extracted together with the opioid agonist and administered parenterally.

The prior art describes several other methods and compositions to minimize the abuse of an opioid containing drug. One such method is discussed in U.S. Pat. No. 6,593,367 (Dewey et al.), describing a method whereby the addiction-related behavior of a mammal suffering from addiction could be changed by a combination of drugs. The method includes administering to the mammal an effective amount of gamma vinyl GABA (GVG) or a pharmaceutically acceptable salt, or an enantiomer or a racemic mixture, where the effective amount is sufficient to diminish, inhibit or eliminate behavior associated with craving or use of the combination of abused drugs.

U.S. Pat. Nos. 4,175,119 and 4,459,278 (Porter et al.) describe compositions and methods useful for the prevention of accidental and/or intentional oral overdoses of a drug.

In summary, various attempts have been made and are described in prior art to develop abuse-deterrent dosage forms. Clearly there is a need for a delivery system for commonly used oral dosage formulations (e.g., immediate release, sustained or extended release and delayed release) of drugs, and in particular analgesics such as opioid analgesics, for patients seeking drug therapy and which deters abuse and minimizes or reduces the potential for physical or psychological dependency.

SUMMARY OF THE INVENTION

The present invention includes a therapeutic pharmaceutical composition including an analgesic, a gel forming polymer, a surfactant, and one or more other excipients.

Some embodiments of the present invention include an extended release abuse deterrent dosage form having a core matrix and PEG applied onto the core matrix. In some embodiments, a core matrix includes a blended mixture of PEO having a molecular weight of from about 300,000 to about 5,000,000; magnesium stearate; and oxycodone or a pharmaceutically acceptable salt thereof. In certain embodiments, the matrix is heated to melt at least a portion of the PEO included in the matrix.

BRIEF DESCRIPTION OF THE DRAWINGS

The present invention will be better understood by examining the following figures which illustrate certain properties of the present invention wherein.

With reference to the Figures, features that are the same across the Figures are denoted with the same reference numbers.

DETAILED DESCRIPTION OF THE INVENTION

The present invention includes an abuse deterrent formulation for reducing the potential for one or more of a) parenteral abuse, b) inhalation (e.g., intranasal abuse), and/or c) oral abuse of a drug, typically an opioid analgesic type drug, for satisfaction of a physical or psychological dependence. In one embodiment, the present invention deters parenteral abuse by providing a pharmaceutical composition which includes an analgesic with one or more gel forming agents such that upon contact with a solvent (e.g., water), the agents swell by absorbing the solvent thereby 1) entrapping the drug in a gel matrix and/or 2) reducing or preventing a significant amount of the opioid analgesic from being drawn into a syringe. In one embodiment, the present invention deters inhalation abuse by providing a pharmaceutical composition which includes a therapeutically active pharmaceutical (e.g., an analgesic), with one or more mucous membrane, mucosa or mucosal tissue irritants (collectively referred to as mucous membrane irritants). In one embodiment, the mucosal tissue is nasal passageway tissue.

Upon contact with a mucous membrane, the irritants induce temporary pain and/or irritation of the membranes and/or tissues to thereby deter abuse. For example, if inhaled by snorting, the mucous membrane in the nasal passageway will be irritated and result in pain to the individual. In one embodiment, the present invention provides a pharmaceutical composition which includes an analgesic with one or more emetics, such that after oral consumption of more than a typically prescribed amount of the dosage form, emesis is induced.

In one embodiment, two or more of the abuse deterrents can be combined into one composition according to the present invention.

Figure 1:
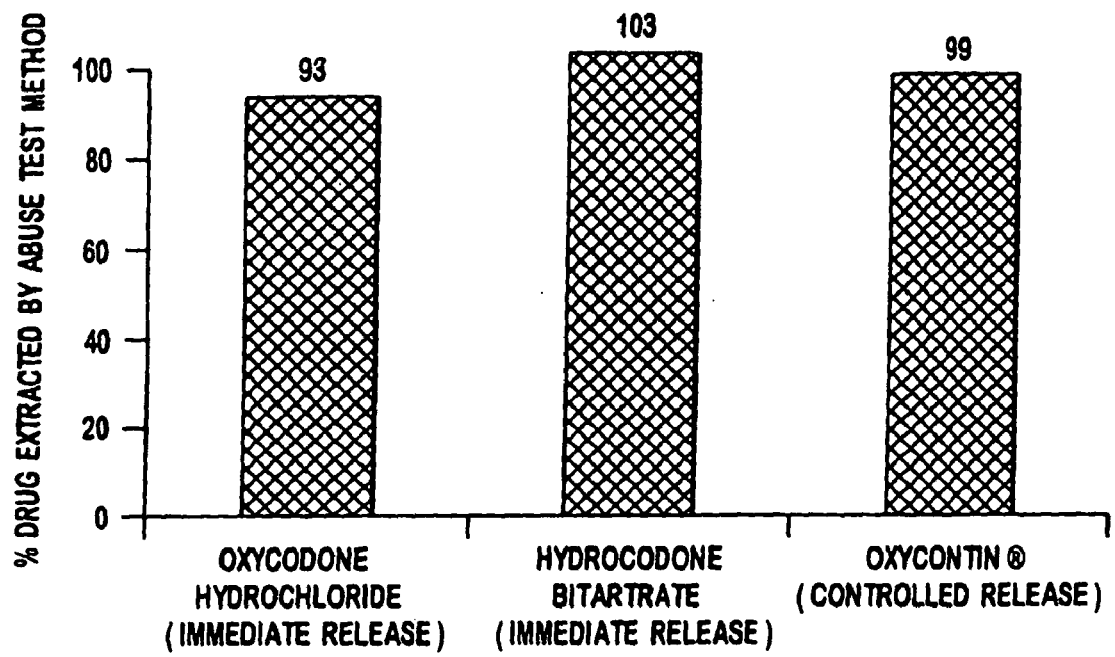
FIG. 1 shows a percentage amount of certain opioid drugs available in solution for injection after standard dosage forms are crushed and exposed to a solvent.
Figure 2:
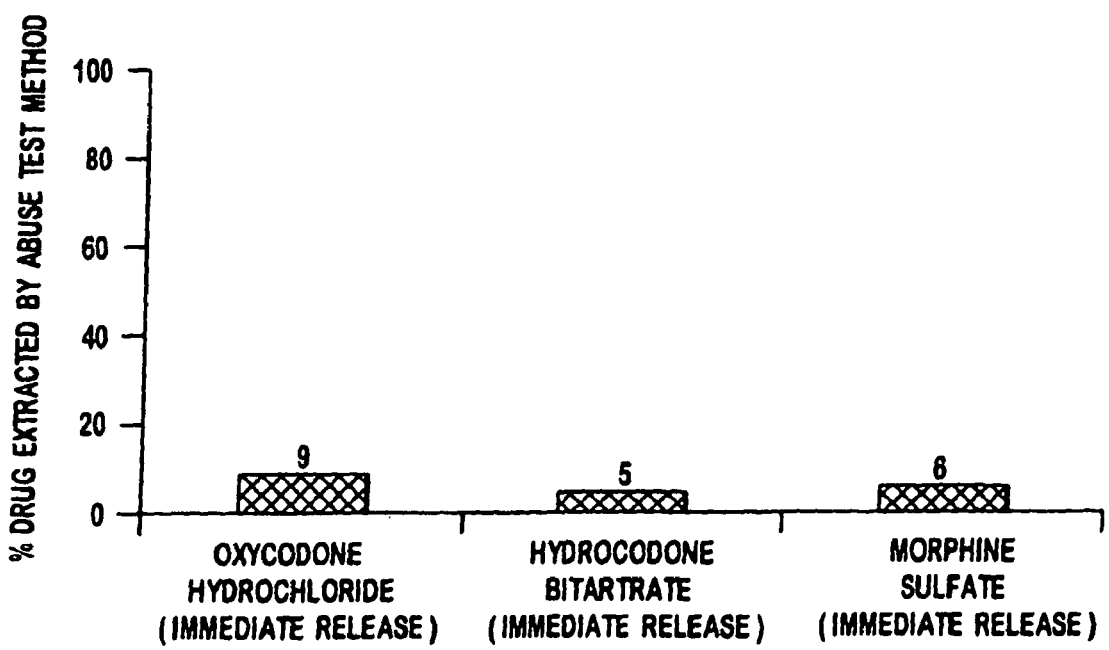
FIG. 2 shows a percentage amount of certain opioid drugs available in solution for injection after dosage forms of the present invention are crushed and exposed to a solvent.

The present invention describes formulations which have abuse deterrent properties as described herein. Examples of specific oral solid dosage forms containing morphine, hydrocodone and oxycodone were evaluated using suitable analytical test methods, such as UV/VIS spectrophotometry. In the evaluation, dosage forms were crushed and contacted with a small amount of water (about a teaspoon or tablespoon). After attempting to dissolve the dosage form, the resultant material was drawn into a syringe, volume was measured and opioid content was quantitated. As shown in FIG. 1, almost 100% of the opioid can be extracted from standard formulations. Comparatively, as shown in FIG. 2, an abuse deterrent formulation of the present invention for the same opioids, provides a significantly lower percentage of extractable opioid. As shown in FIG. 1, approximately 93%, 103% and 99% of the opioid analgesic drugs contained in a dosage form were recoverable using the above described techniques. Comparatively, as shown in FIG. 2, using an abuse deterrent polymer of the present invention, only 9%, 5%, and 6% of the opioid analgesic drugs were recoverable.

In another embodiment, the present invention is a pharmaceutical composition that includes an opioid analgesic, one or more gel forming agents, and one or more mucous membrane irritants or nasal passageway tissue irritants. In another embodiment, the present invention includes a pharmaceutical composition, which includes an analgesic, one or more gel forming agents and one or more emetics as described herein. In another embodiment, the present invention includes a pharmaceutical composition, which includes an opioid analgesic, one or more mucous membrane irritants or nasal passageway tissue irritants and one or more emetics as described herein. In one particular embodiment, the present invention includes a pharmaceutical composition which includes an analgesic, one or more gel forming agents, one or more mucous membrane irritants and/or nasal passageway tissue irritants, and one or more emetics.

Each of the components of the pharmaceutical composition of the present invention are described in more detail below.

A. Drugs Suitable for Use with the Present Invention

Any drug, therapeutically acceptable drug salt, drug derivative, drug analog, drug homologue, or polymorph can be used in the present invention. In one embodiment, the drug can be orally administered. In certain embodiments, drugs susceptible to abuse are used. Drugs commonly susceptible to abuse include psychoactive drugs and analgesics, including but not limited to opioids and drugs that can cause psychological and/or physical dependence on the drug.

A drug for use in the present invention can be one or more of the following: alfentanil, amphetamines, buprenorphine, butorphanol, carfentanil, codeine, dezocine, diacetylmorphine, dihydrocodeine, dihydromorphine, diphenoxylate, diprenorphine, etorphine, fentanyl, hydrocodone, hydromorphone, β-hydroxy-3-methylfentanyl, levo-α-acetylmethadol, levorphanol, lofentanil, meperidine, methadone, methylphenidate, morphine, nalbuphine, nalmefene, o-methylnaltrexone, naloxone, naltrexone, oxycodone, oxymorphone, pentazocine, pethidine, propoxyphene, remifentanil, sufentanil, tilidine and tramodol, salts, derivatives, analogs, homologues, polymorphs thereof, and mixtures of any of the foregoing.

In one embodiment, a pharmaceutical composition of the present invention includes one or more opioids such as hydrocodone, morphine and oxycodone and/or salts thereof, as the therapeutically active ingredient. Typically when processed into a suitable dosage form, as described in more detail below, the drug can be present in such dosage forms in an amount normally prescribed, typically about 0.5 to about 25 percent on a dry weight basis, based on the total weight of the formulation.

With respect to analgesics in unit dose form, such an amount can be typically from about 5, 25, 50, 75, 100, 125, 150, 175 or 200 mg. More typically, the drug can be present in an amount from 5 to 500 mg or even 5 to 200 mg. In other embodiments, a dosage form contains an appropriate amount of drug to provide a therapeutic effect.

B. Gel Forming Agents

As described above, the present invention can include one or more gel forming agents. The total amount of gel forming agent is typically about 3 to about 40 percent on a dry weight basis of the composition.

Suitable gel forming agents include compounds that, upon contact with a solvent (e.g., water), absorb the solvent and swell, thereby forming a viscous or semi-viscous substance that significantly reduces and/or minimizes the amount of free solvent which can contain an amount of solublized drug, and which can be drawn into a syringe. The gel can also reduce the overall amount of drug extractable with the solvent by entrapping the drug in a gel matrix. In one embodiment, typical gel forming agents include pharmaceutically acceptable polymers, typically hydrophilic polymers, such as hydrogels.

In some embodiments, the polymers exhibit a high degree of viscosity upon contact with a suitable solvent. The high viscosity can enhance the formation of highly viscous gels when attempts are made by an abuser to crush and dissolve the contents of a dosage form in an aqueous vehicle and inject it intravenously.

More specifically, in certain embodiments the polymeric material in the present invention provides viscosity to the dosage form when it is tampered. In such embodiments, when an abuser crushes and dissolves the dosage form in a solvent (e.g., water or saline), a viscous or semi-viscous gel is formed. The increase in the viscosity of the solution discourages the abuser from injecting the gel intravenously or intramuscularly by preventing the abuser from transferring sufficient amounts of the solution to a syringe to cause a desired "high" once injected.

Suitable polymers include one or more pharmaceutically acceptable polymers selected from any pharmaceutical polymer that will undergo an increase in viscosity upon contact with a solvent. Preferred polymers include polyethylene oxide, polyvinyl alcohol, hydroxypropyl methyl cellulose and carbomers. In preferred embodiments, the polymers include:

a) Polyethylene Oxide

In some embodiments, the polymer includes polyethylene oxide. The polyethylene oxide can have an average molecular weight ranging from about 300,000 to about 5,000,000, more preferably from about 600,000 to about 5,000,000, and most preferably at least about 5,000,000. In one embodiment, the polyethylene oxide includes a high molecular weight polyethylene oxide.

In one embodiment, the average particle size of the polyethylene oxide ranges from about 840 to about 2,000 microns. In another embodiment, the density of the polyethylene oxide can range from about 1.15 to about 1.26 g/ml. In another embodiment, the viscosity can range from about 8,800 to about 17,600 cps.

The polyethylene oxide used in a directly compressible formulation of the present invention is preferably a homopolymer having repeating oxyethylene groups, i.e., $-(-O-CH_2-CH_2-)_n-$, where n can range from about 2,000 to about 180,000. Preferably, the polyethylene oxide is a commercially available and pharmaceutically acceptable homopolymer having moisture content of no greater than about 1% by weight. Examples of suitable, commercially available polyethylene oxide polymers include Polyox®, WSRN-1105 and/or WSR-coagulant, available from Dow chemicals.

In some embodiments, the polyethylene oxide powdered polymers can contribute to a consistent particle size in a directly compressible formulation and eliminate the problems of lack of content uniformity and possible segregation.

b) Polyvinyl Alcohol

In one embodiment, the gel forming agent includes polyvinyl alcohol. The polyvinyl alcohol can have a molecular weight ranging from about 20,000 to about 200,000. The specific gravity of the polyvinyl alcohol can range from about 1.19 to about 1.31 and the viscosity from about 4 to about 65 cps. The polyvinyl alcohol used in the formulation is preferably a water-soluble synthetic polymer represented by $-(-C_2H_4O-)_n-$, where n can range from about 500 to about 5,000. Examples of suitable, commercially available polyvinyl alcohol polymers include PVA, USP, available from Spectrum Chemical Manufacturing Corporation, New Brunswick, N.J. 08901.

c) Hydroxypropyl Methyl Cellulose

In one embodiment, the gel forming agent includes hydroxypropyl methyl cellulose (Hypromellose). The hydroxypropyl methyl cellulose can have a molecular weight ranging from about 10,000 to about 1,500,000, and typically from about 5000 to about 10,000, i.e., a low molecular weight hydroxypropyl methyl cellulose polymer. The specific gravity of the hydroxypropyl methyl cellulose can range from about 1.19 to about 1.31, with an average specific gravity of about 1.26 and a viscosity of about 3600 to 5600. The hydroxypropyl methyl cellulose used in the formulation can be a water-soluble synthetic polymer. Examples of suitable, commercially available hydroxypropyl methylcellulose polymers include Methocel K100 LV and Methocel K4M, available from Dow chemicals.

d) Carbomers

In one embodiment, the present invention includes carbomers. The carbomers can have a molecular weight ranging from 700,000 to about 4,000,000,000. The viscosity of the polymer can range from about 4000 to about 39,400 cps. Examples of suitable, commercially available carbomers include carbopol 934P NF, carbopol 974P NF and carbopol 971P NF, available from Noveon Pharmaceuticals.

Following the teachings set forth herein, other suitable gel forming agents can include one or more of the following polymers: ethyl cellulose, cellulose acetate, cellulose acetate propionate, cellulose acetate butyrate, cellulose acetate phthalate and cellulose triacetate, cellulose ether, cellulose ester, cellulose ester ether, and cellulose, acrylic resins comprising copolymers synthesized from acrylic and methacrylic acid esters, the acrylic polymer may be selected from the group consisting of acrylic acid and methacrylic acid copolymers, methyl methacrylate copolymers, ethoxyethyl methacrylates, cyanoethyl methacrylate, poly(acrylic acid), poly (methaerylic acid), methacrylic acid alkylamide copolymer, poly(methyl methacrylate), polymethacrylate, poly(methyl methacrylate) copolymer, polyacrylamide, aminoalkyl methacrylate copolymer, poly(methacrylic acid anhydride), and glycidyl methacrylate copolymers.

Any of the above described polymers can be combined together or combined with other suitable polymers, and such combinations are within the scope of the present invention.

Figure 3:
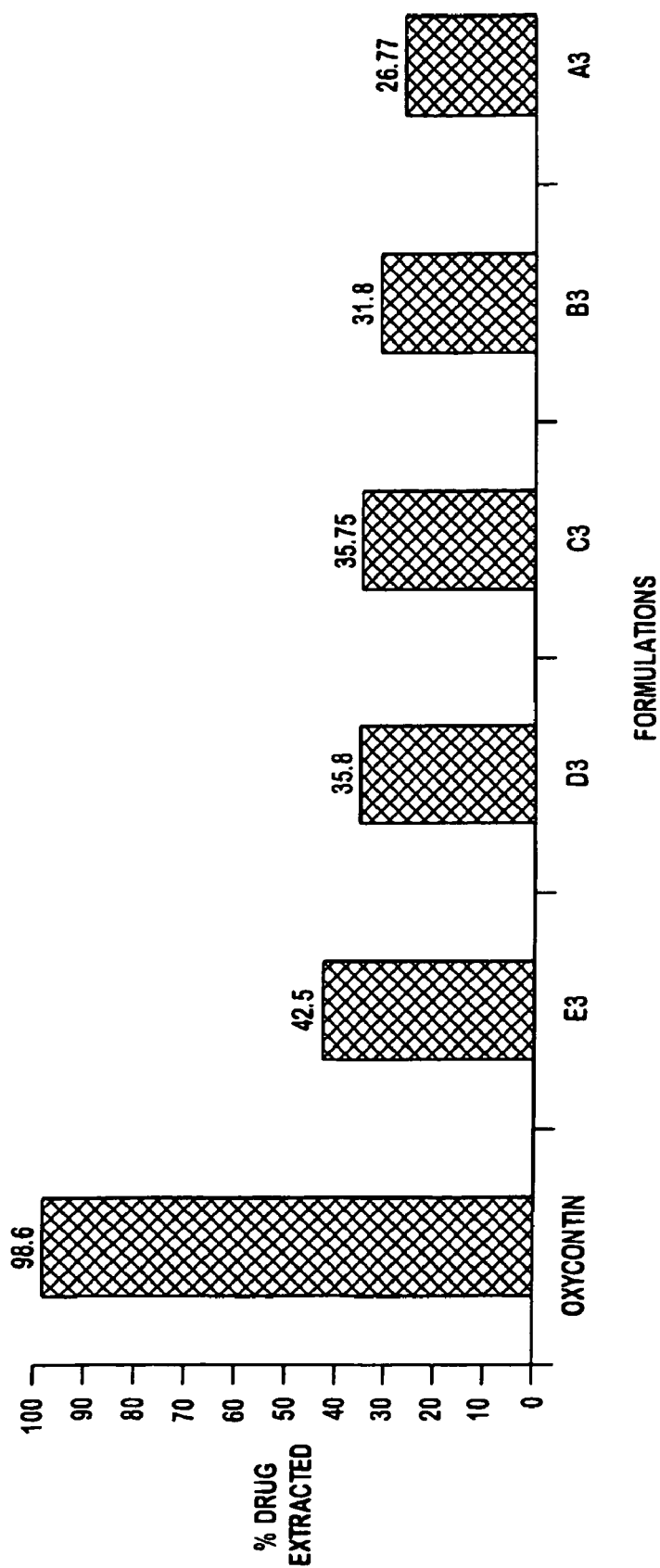
FIG. 3 shows an amount of drug recoverable from a solvent contacted with five embodiments of the present invention compared to a standard formulation.

In one embodiment, the abuse deterrent, gel forming agent can prevent less than or equal to about 95%, 94%, 70%, 60%, 54%, 50%, 45%, 40%, 36%, 32%, 30%, 27%, 20%, 10%, 9%, 6%, 5% or 2% of the total amount of drug in a dosage form from being recovered from a solvent in contact with a dosage form of the present invention. As shown in FIG. 3, formulations A3, B3, C3, D3 and E3 reduce the amount of drug extractable or recoverable from a dosage for of the present invention. Specifically, formulation A3 provides for recovery of 26.77% of the total amount of drug in the dosage form, formulation B3 provides for recovery of 31.8% of the total amount of drug in the dosage form, formulation C3 provides for recovery of 35.75% of the total amount of drug in the dosage form, formulation D3 provides for recovery of 35.8% of the total amount of drug in the dosage form, and formulation E3 provides for recovery of 42.5% of the total amount of drug in the dosage form. In FIG. 3, all five formulations A3 through E3 are compared with a standard dosage form of oxycontin, which provided for recovery of 98.6% of the total amount of drug in the dosage form.

The five formulations A3 through E3 are set forth in Examples 14 through 18, respectively.

Figure 4:
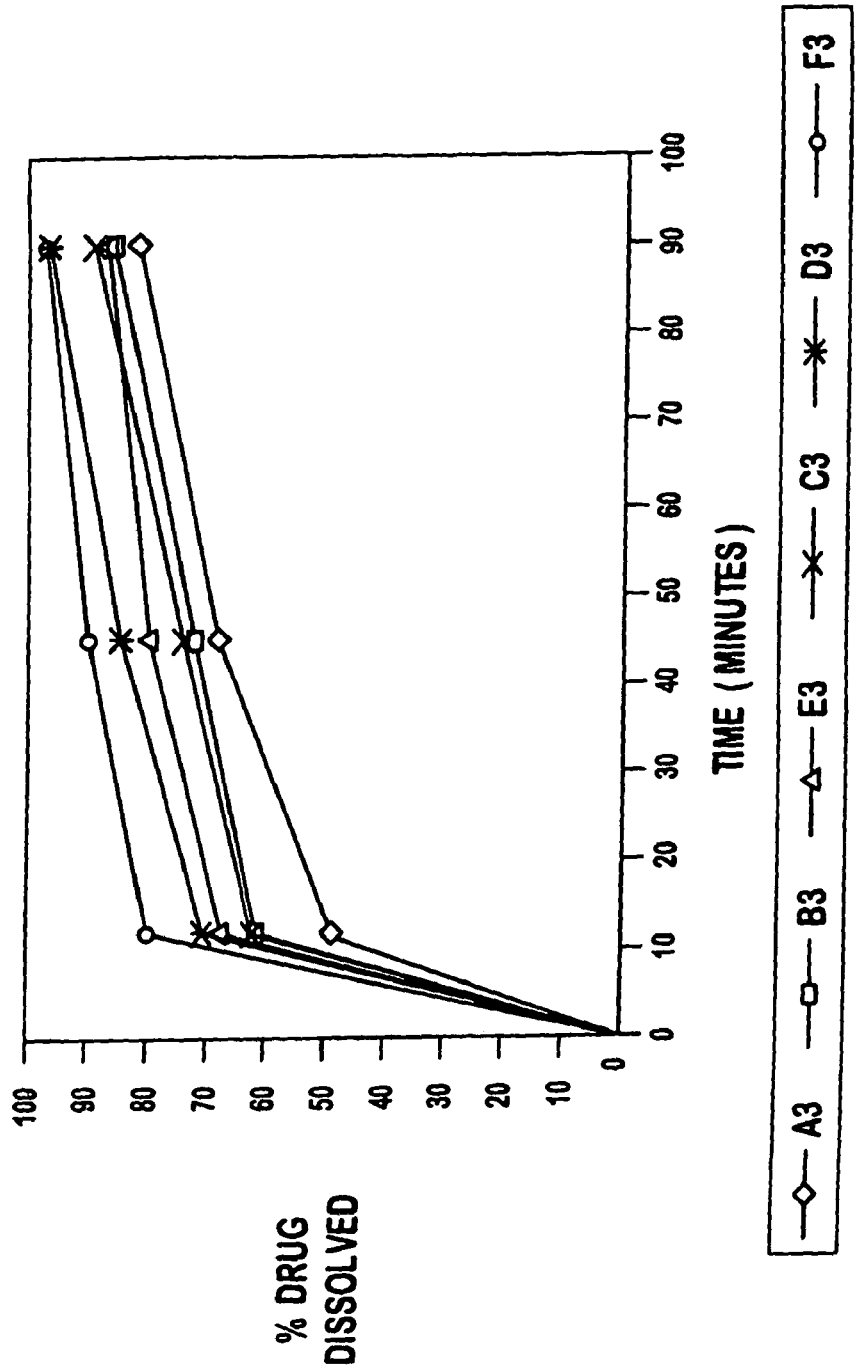
FIG. 4 shows a dissolution profile of six embodiments of the present invention.

It should be noted that the above described formulations also have dissolution profiles as determined by the USP 2-paddle method, as shown in FIG. 4. In particular, for formulations A3 through E3, about 50% to about 82% of each formulation dissolves after about 15 minutes and about 80% to about 95% dissolves after 90 minutes. FIG. 4 further includes the dissolution profile of Formulation F3. With respect to FIG. 4, the composition of formulation F3 is set forth in Example 19.

The above described gel forming agents can be further optimized as necessary or desired in terms of viscosity, molecular weight, etc.

C. Mucous Membrane Irritants and/or Nasal Passageway Tissue Irritants

As described above, the present invention can include one or more mucous membrane irritants and/or nasal passageway tissue irritants. In one embodiment, suitable mucous membrane irritants and/or nasal passageway tissue irritants include compounds that are generally considered pharmaceutically inert, yet can induce irritation. Such compounds include, but are not limited to surfactants. In one embodiment, suitable surfactants include sodium lauryl sulfate, poloxamer, sorbitan monoesters and glyceryl monooleates. Other suitable compounds are believed to be within the knowledge of a practitioner skilled in the relevant art, and can be found in the Handbook of Pharmaceutical Excipients, 4th Ed. (2003), the entire content of which is hereby incorporated by reference.

In one embodiment of the present invention, the irritant can be present in amount of from 1 to 20 percent by weight on a solid basis, preferably 1 to 10 percent by weight on a solid basis. In another embodiment, the amount of irritant can be present in an amount of 5 to 15 percent by weight. In another embodiment, the irritant can be present in an amount of at least 5 percent by weight. In yet another embodiment, the irritant can be present in an amount from 1 to 5 percent by weight. In another embodiment, the amount of irritant can be present in an amount from 1 to 3 percent by weight.

In certain embodiments, the irritant can deter abuse of a dosage form when a potential abuser tampers with a dosage form of the present invention. Specifically, in such embodiments, when an abuser crushes the dosage form, the irritant is exposed. The irritant discourages inhalation of the crushed dosage form by inducing pain and/or irritation of the abuser's mucous membrane and/or nasal passageway tissue. In one embodiment, the irritant discourages inhalation (e.g., via snorting through the nose) by inducing pain and/or irritation of the abuser's nasal passageway tissue.

In one embodiment, the present invention includes one or more mucous membrane irritants to cause irritation of mucous membranes located anywhere on or in the body, including membranes of the mouth, eyes and intestinal tract. Such compositions can deter abuse via oral, intra-ocular or rectal or vaginal routes.

The above-described irritants can be further optimized as necessary or desired in terms of concentration, irritation severity, etc.

D. Emetics

As described above, the present invention can include one or more emetics or emesis inducing agents. Preferably, the emetic is a pharmaceutically acceptable inert excipient that only induces emesis after a certain threshold amount is ingested. In another embodiment, the emetic can be a pharmaceutically active emetic.

In one embodiment, the amount of emetic present in a pharmaceutical composition of the present invention can be tied directly to the amount of drug in the pharmaceutical composition. Thus, by controlling the quantity of the emetic compound in the pharmaceutical composition, emesis can be avoided if normal prescription directions are followed. However, if an overdosage occurs by ingesting more than a prescribed quantity of a drug in a pharmaceutical composition of the present invention, the amount of ingested emetic can exceed the threshold amount necessary to induce emesis.

In some embodiments, the threshold amount of emetic for inducing emesis can be reached when the normal prescription directions are inappropriately increased by factors of 2, 3, 4, 5, 6, 7, or 8 times, or more. Thus, in some embodiments, the amount of emetic present in a pharmaceutical composition of the present invention is an amount such that the amount of emetic ingested does not exceed the threshold amount necessary for inducing emesis until a subject ingests 2, 3, 4, 5, 6, 7, or 8 or more times the amount of drug normally prescribed. In some embodiments, emesis can preclude death or serious illness in the subject.

In one embodiment, the emetic includes zinc sulfate. Zinc sulfate is an excipient, which can induce emesis when more than about 0.6 to 2.0 gm is ingested, typically more than about 0.6 gm. In one embodiment, a pharmaceutically acceptable inert excipient which can induce emesis (e.g., zinc sulfate) can be present at about 5 to 60 percent by weight on a solid basis, or about 5 to 40 percent by weight on a solid basis or about 5 to 25 percent by weight on a solid basis more typically about 5 to 10 percent by weight on a solid basis.

Accordingly, pharmaceutical compositions of the present invention can be easily designed to induce emesis if a prescribed dosage is exceeded and/or if prescription directions are not followed for dosage forms containing a composition of the present invention. In some embodiments of the present invention, a dosage form can include about 0.01, 0.05, 0.1, 0.15, 0.2, 0.25, 0.3, 0.35, 0.4, 0.45, 0.5, 0.55, 0.6, 0.65, 0.7, 0.75, 0.8, 0.85, 0.90, 0.95, 1.0 grams of a pharmaceutically acceptable inert excipient which can induce emesis (e.g., zinc sulfate) or pharmaceutically active emetic. In another embodiment, the present invention includes an inert excipient which can induce emesis (e.g., zinc sulfate) or pharmaceutically active emetic in an amount that is a summation of two or more of the above described amounts.

In another embodiment, the present invention can include 1, 2, 3, 4, or 5 times, or more, of the above described amounts of pharmaceutically acceptable inert excipient which can induce emesis (e.g., zinc sulfate) or a pharmaceutically active emetic. Typically, suitable embodiments of the present invention include from about 0.1 gm to about 2.0 gm of zinc sulfate. In other embodiments the present invention can include about 0.6 to less than about 2.0 gm of zinc sulfate.

For example, in one embodiment, if a practitioner desires to create a dosage form that will induce emesis only after four or more dosage forms are ingested, the amount of zinc sulfate in each dosage form should not exceed about 0.19 gm. Thus, if three dosage forms are ingested, the amount of emetic is 0.57 gm, which is less than a typical threshold amount of the particular emetic. However, if a fourth dosage form having 0.19 gm. of zinc sulfate is ingested, the amount of emetic exceeds the threshold amount, and emesis is induced.

The above-described emetics can be further optimized as necessary or desired in terms of concentration in the pharmaceutical composition, etc.

Other suitable emetics can include one or more of cephaeline, methyl cephaeline, psychotrine, O-methylpsychotrine, ammonium chloride, potassium chloride, magnesium sulfate, ferrous gluconate, ferrous sulfate, aloin, and emetine.

E. Other Ingredients

The present invention can also optionally include other ingredients to enhance dosage form manufacture from a pharmaceutical composition of the present invention and/or alter the release profile of a dosage forming including a pharmaceutical composition of the present invention.

Some embodiments of the present invention include one or more pharmaceutically acceptable fillers/diluents. In one embodiment, Avicel PH (Microcrystalline cellulose) is a filler used in the formulation. The Avicel PH can have an average particle size ranging from 20 to about 200 μm, preferably about 100 μm. The density ranges from 1.512-1.668 g/cm$^3$. The Avicel PH should have molecular weight of about 36,000. Avicel PH effectiveness is optimal when it is present in an amount of from about 10 to 65 percent, by weight on a solid basis, of the formulation. Typical fillers can be present in amounts from 10 to 65 percent by weight on a dry weight basis. Other ingredients can include sugars and/or polyols.

Other ingredients can also include dibasic calcium phosphate having a particle size of about 75 to about 425 microns and a density of about 0.5 to about 1.5 g/ml, as well as calcium sulfate having a particle size of about 1 to about 200 microns and a density of about 0.6 to about 1.3 g/ml and mixtures thereof. Further, lactose having a particle size of about 20 to about 400 microns and a density of about 0.3 to about 0.9 g/ml can also be included.

In some embodiments of the invention, the fillers which can be present at about 10 to 65 percent by weight on a dry weight basis, also function as binders in that they not only impart cohesive properties to the material within the formulation, but can also increase the bulk weight of a directly compressible formulation (as described below) to achieve an acceptable formulation weight for direct compression. In some embodiments, additional fillers need not provide the same level of cohesive properties as the binders selected, but can be capable of contributing to formulation homogeneity and resist segregation from the formulation once blended. Further, preferred fillers do not have a detrimental effect on the flowability of the composition or dissolution profile of the formed tablets.

In one embodiment, the present invention can include one or more pharmaceutically acceptable disintegrants. Such disintegrants are known to a skilled artisan. In the present invention, disintegrants can include, but are not limited to, sodium starch glycolate (Explotab®) having a particle size of about 104 microns and a density of about 0.756 g/ml, starch (e.g., Starch 21) having a particle size of about 2 to about 32 microns and a density of about 0.462 g/ml, Crospovidone® having a particle size of about 400 microns and a density of about 1.22 g/ml, and croscarmellose sodium (Ac-Di-Sol) having a particle size of about 37 to about 73.7 microns and a density of about 0.529 g/ml. The disintegrant selected should contribute to the compressibility, flowability and homogeneity of the formulation. Further the disintegrant can minimize segregation and provide an immediate release profile to the formulation. In some embodiments, the disintegrant(s) are present in an amount from about 2 to about 25 percent by weight on a solid basis of the directly compressible formulation.

In one embodiment, the present invention can include one or more pharmaceutically acceptable glidants, including but not limited to colloidal silicon dioxide. In one embodiment, colloidal silicon dioxide (Cab-O-Sil®) having a density of about 0.029 to about 0.040 g/ml can be used to improve the flow characteristics of the formulation. Such glidants can be provided in an amount of from about 0.1 to about 1 percent by weight of the formulation on a solid basis. It will be understood, based on this invention, however, that while colloidal silicon dioxide is one particular glidant, other glidants having similar properties which are known or to be developed could be used provided they are compatible with other excipients and the active ingredient in the formulation and which do not significantly affect the flowability, homogeneity and compressibility of the formulation.

In one embodiment, the present invention can include one or more pharmaceutically acceptable lubricants, including but not limited to magnesium stearate. In one embodiment, the magnesium stearate has a particle size of about 450 to about 550 microns and a density of about 1.00 to about 1.80 g/ml. In one embodiment, magnesium stearate can contribute to reducing friction between a die wall and a pharmaceutical composition of the present invention during compression and can ease the ejection of the tablets, thereby facilitating processing. In some embodiments, the lubricant resists adhesion to punches and dies and/or aid in the flow of the powder in a hopper and/or into a die. In an embodiment of the present invention, magnesium stearate having a particle size of from about 5 to about 50 microns and a density of from about 0.1 to about 1.1 g/ml is used in a pharmaceutical composition. In certain embodiments, a lubricant should make up from about 0.1 to about 2 percent by weight of the formulation on a solids basis. Suitable lubricants are stable and do not polymerize within the formulation once combined. Other lubricants known in the art or to be developed which exhibit acceptable or comparable properties include stearic acid, hydrogenated oils, sodium stearyl fumarate, polyethylene glycols, and Lubritab®.

In certain embodiments, the most important criteria for selection of the excipients are that the excipients should achieve good content uniformity and release the active ingredient as desired. The excipients, by having excellent binding properties, and homogeneity, as well as good compressibility, cohesiveness and flowability in blended form, minimize segregation of powders in the hopper during direct compression.

In another embodiment, the present invention can include an opioid antagonist in addition to the other ingredients, or as a substitute for one of the other abuse deterrent ingredients of a formulation of the present invention. Suitable antagonists are described above. One particular antagonist includes naloxone. As described above, typically naloxone has no action when taken orally, and will not interfere with the pharmacologic action of an opioid agonist. However, when given by injection naloxone can have profound antagonistic action to opioid agonists. An appropriate antagonist can be used in combination with one or more of gel forming agents, mucous membrane irritants and/or nasal passageway tissue irritants, or emetics in the present invention. An appropriate antagonist can also be used as a substitute for one or more of gel forming agents, mucous membrane irritants and/or nasal passageway tissue irritants, or emetics in the present invention. Suitable opioid receptor antagonists can include but are not limited to the antagonists described in U.S. Pat. Nos. 6,559,159 and 6,375,957, the entire content of which are hereby incorporated by reference.

F. Dosage Forms of the Present Invention

A pharmaceutical composition of the present invention including one or more drug components, one or more of gel forming agents, mucous membrane irritants and/or nasal passageway tissue irritants, and emetics, and optionally other ingredients, can be suitably modified and processed to form a dosage form of the present invention. As referred to herein and in FIGS. 5a, 5b, 5c and 6, an "abuse deterrent composition" or "ADC" (labeled "40" in these Figures) includes a composition having one or more gel forming agents and/or mucous membrane irritants and/or nasal passageway tissue irritants, and/or emetics according to the teachings set forth herein. In this manner, an abuse deterrent composition can be layered onto, coated onto, applied to, admixed with, formed into a matrix with, and/or blended with a drug and optionally other ingredients, thereby providing a therapeutic composition of the present invention.

Figure 5A:
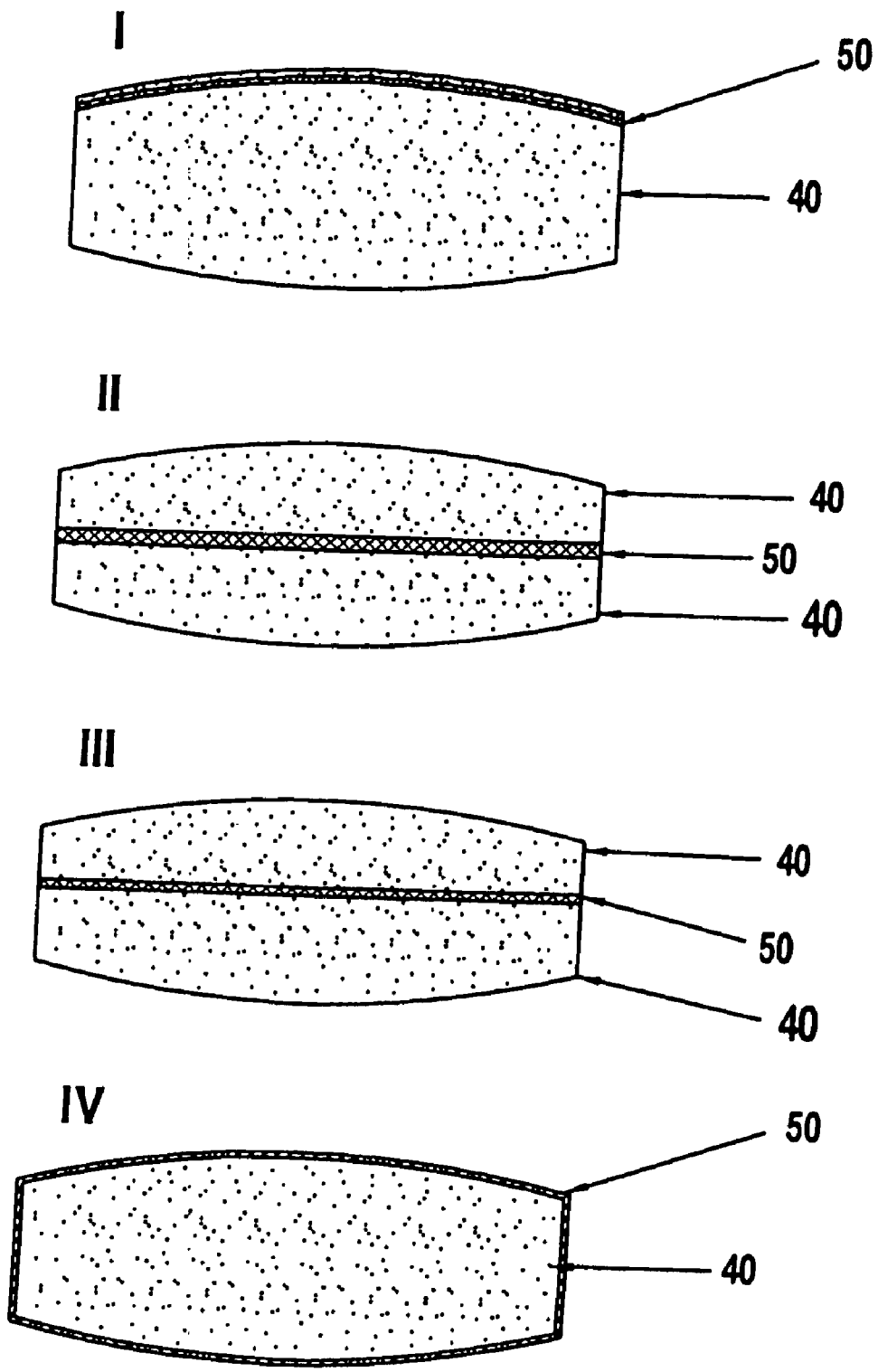
FIG. 5a shows various methods used to formulate the dosage forms having one or more abuse deterrent properties of the present invention.

As shown in FIG. 5a, an abuse deterrent composition can be combined with a drug and/or opioid analgesic (e.g., hydrocodone) in one or more layered dosage forms. According to the present invention, drug 50 can be a layer on or near the surface (I) of ADC 40 of the present invention, or sandwiched between two or more distinct layers (II and III) of ADC 40 of the present invention. In other embodiments, drug 50 can be a coating (IV) on ADC 40. Drug 50 can be any of the pharmaceutically active ingredients (e.g., opioids) described herein and can be combined with other excipients, e.g. disintegrants including but not limited to sodium starch glycolate or Explotab®.

Figure 5B:
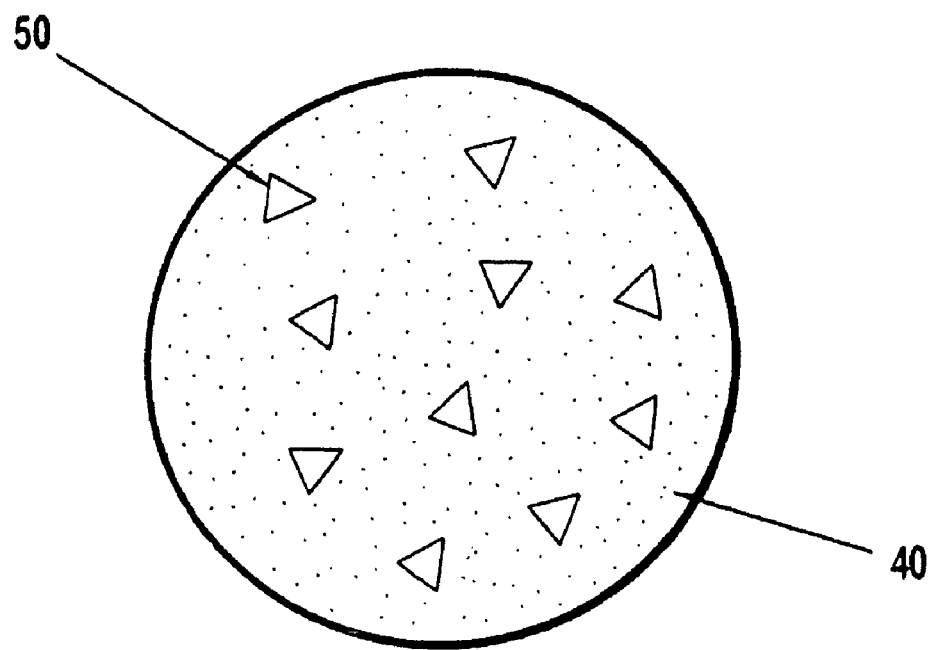
FIG. 5b shows a particular dosage form having one or more abuse deterrent properties of the present invention.

As shown in FIG. 5b an abuse deterrent composition 40 of the present invention can be combined with drug 50, e.g., hydrocodone, in a blended mixture. In such embodiments, drug 50 and ADC 40 can be evenly mixed.

Figure 5C:
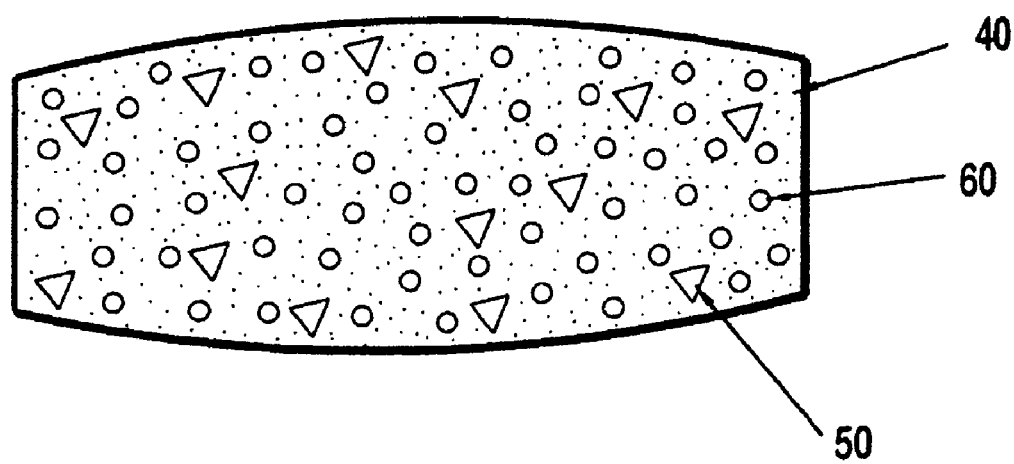
FIG. 5c shows a particular dosage form having one or more abuse deterrent properties of the present invention and a disintegrant.

As shown in FIG. 5c abuse deterrent composition 40 of the present invention can be combined with drug 50, e.g., hydrocodone, in a blended mixture with other ingredients 60, e.g., a disintegrant.

Figure 6:
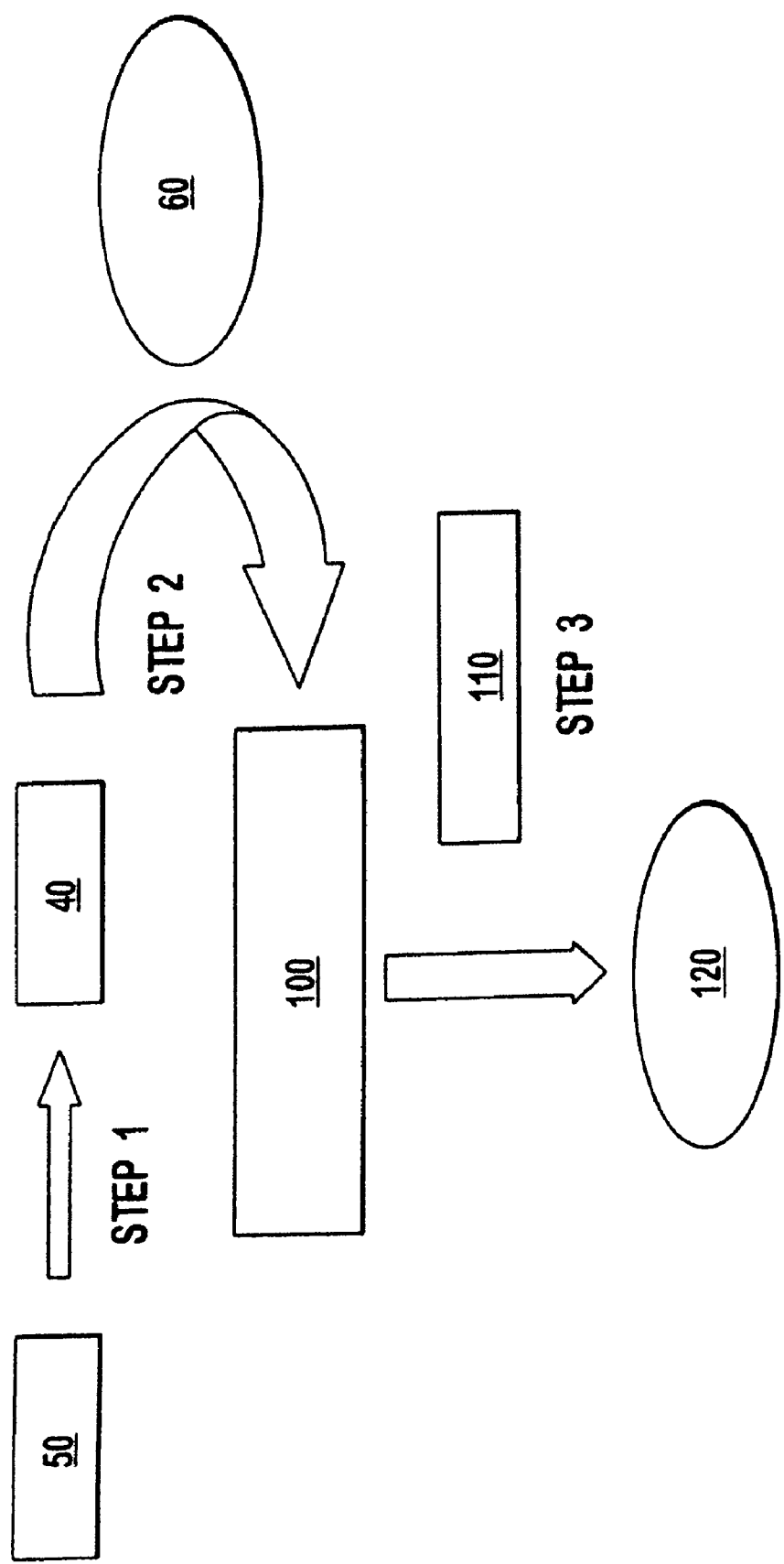
FIG. 6 shows a process flow chart for the manufacture of a dosage form of the present invention.

FIG. 6 shows one embodiment of the present invention for making a dosage form of the present invention. Specifically, a first step (step 1) of FIG. 4 shows drug 50 combined with abuse deterrent composition 40 of the present invention. ADC 40 can contain one or more gel forming agents and/or mucous membrane irritants and/or nasal passageway tissue irritants, and/or emetics according to the teachings set forth herein. In a second step (step 2), the combination of drug 50 and ADC 40 can then be blended with other ingredients 60, e.g. disintegrants and lubricants, to form a mix 100. Lastly, in a third step (step 3) combination 100 can then be processed using conventional practices 110, e.g., compression, into a suitable unit dosage form 120, e.g. tablets.

Suitable formulations and dosage forms of the present invention include but are not limited to powders, caplets, pills, suppositories, gels, soft gelatin capsules, capsules and compressed tablets manufactured from a pharmaceutical composition of the present invention. The dosage forms can be any shape, including regular or irregular shape depending upon the needs of the artisan.

Compressed tablets including the pharmaceutical compositions of the present invention can be direct compression tablets or non-direct compression tablets. In one embodiment, a dosage form of the present invention can be made by wet granulation, and dry granulation (e.g., slugging or roller compaction). The method of preparation and type of excipients are selected to give the tablet formulation desired physical characteristics that allow for the rapid compression of the tablets. After compression, the tablets must have a number of additional attributes such as appearance, hardness, disintegrating ability, and an acceptable dissolution profile.

Choice of fillers and other excipients typically depend on the chemical and physical properties of the drug, behavior of the mixture during processing, and the properties of the final tablets. Adjustment of such parameters is understood to be within the general understanding of one skilled in the relevant art. Suitable fillers and excipients are described in more detail above.

The manufacture of a dosage form of the present invention can involve direct compression and wet and dry granulation methods, including slugging and roller compaction. However, in the present invention, it is preferred to use direct compression techniques because of the lower processing time and cost advantages.

Accordingly, and as described further below, a directly compressible pharmaceutical composition of the present invention can be designed following the teachings set forth herein that can deter one or more of a) parenteral abuse of a drug, b) inhalation abuse of a drug, and c) oral abuse of a drug.

Such compositions and dosage forms are formed according to the present invention are described. Steps for making the compositions or dosage forms include the step of providing one or more drugs and/or analgesics described above and an amount of a gel forming polymer having a desired molecular weight or viscosity as described above, and/or providing a nasal tissue irritant, and/or providing an emetic in the amounts as described above.

By controlling the molecular weight and/or viscosity of the gel forming polymer, and/or by controlling the amount of mucous membrane irritant and/or nasal tissue irritant such that nasal tissue irritation occurs if the composition is inhaled (e.g. snorting), and/or by controlling the amount of emetic such that emesis ensues if more than a prescribed amount of the analgesic is consumed, a therapeutic composition suitable for use to deter drug abuse can be formed. The compositions according to the present invention can deter abuse of the analgesic by (1) forming a viscous substance upon contact with a solvent such that the substance and analgesic cannot be easily drawn into a syringe and/or (2) by inducing mucous membrane irritation and/or nasal tissue irritation if the composition is inhaled, and/or (3) by inducing emesis if more than a prescribed amount of the analgesic is consumed.

Figure 7:
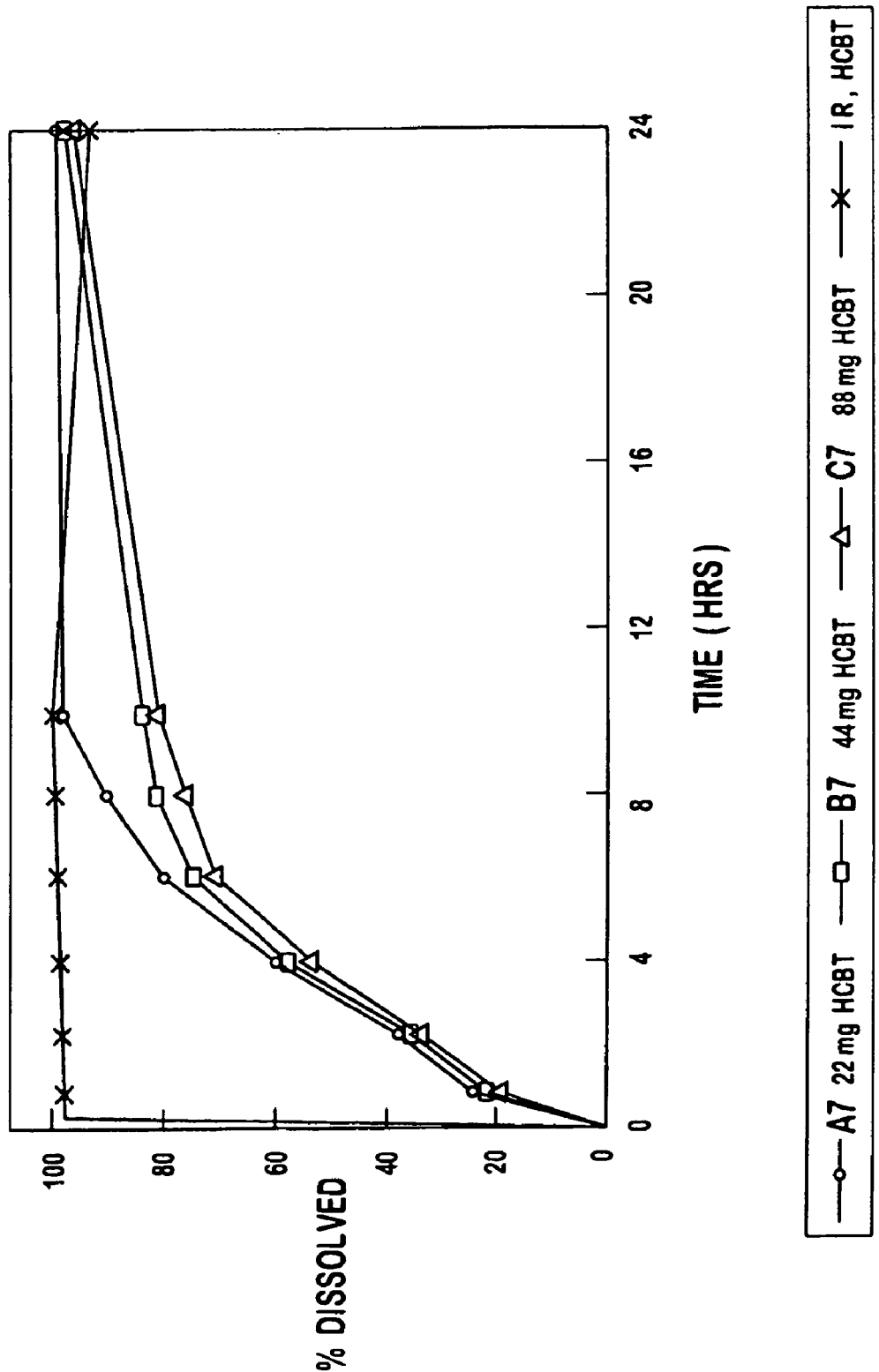
FIG. 7 shows a dissolution profile of three extended release formulations of the present invention.

The present invention can be used to manufacture immediate release, and controlled drug release formulations. Controlled release formulations can include delayed release and extended release oral solid dosage preparations. Examples 25 (formulation A7 of FIG. 7), 26 (formulation B7 of FIG. 7) and 27 (formulation C7 of FIG. 7) provide embodiments of the invention that can provide controlled release of a drug. The release profiles of the controlled release dosage forms of the present invention are shown in FIG. 7. The dosage forms in FIG. 7 include hydrocodone bitartrate (HCBT) as an active. As shown in FIG. 7, about 80 to 95% of the drug in a controlled release dosage form of the present invention is released after about 10 hours, as compared to an immediate release dosage form (a conventional dosage form) which is at least 75% dissolved after about 45 minutes. Other opioid formulations having an extended effect, which can be modified to further include one or more of the abuse deterrent compositions of the present invention, are described in U.S. Pat. No. 6,572,885, the entire content of which is hereby incorporated by reference.

For example, embodiments of the present invention may be prepared via melt techniques. In certain embodiments the opioid may be combined with one or more polymers of the present invention and optionally other ingredients to form a homogenous mixture and then the mixture can be subjected to a temperature for a duration sufficient to melt at least a portion of the polymer.

Sustained release matrices can also be prepared via melt-granulation or melt-extrusion techniques. In some embodiments, melt-granulation techniques involve melting a normally solid material and incorporating a powdered drug therein. In some embodiments, a homogenous mixture may be heated to a temperature sufficient to at least soften the mixture sufficiently to extrude the same.

Certain aspects of the present invention may be better understood as illustrated by the following examples, which are meant by way of illustration and not limitation.

Example 1

A direct compression formulation, as shown in Table 1, for an immediate release opioid analgesic, e.g. hydrocodone bitartrate, tablet having 5 mg of hydrocodone bitartrate was formed by weighing each component separately and mixing the hydrocodone bitartrate and the polymer in a V-blender for about 5 to 10 minutes at low shear conditions or in a high shear blender by mixing 2 to 5 minutes. The other formulation excipients were added to the above blend excepting the lubricant and mixed at the same rate for additional 5 to about 10 minutes. Finally, the lubricant, magnesium stearate was added to the formulation and blended at the same rate for an additional 3 to 5 minutes. This polymeric matrix containing the drug and other excipients was further compressed on a rotary tablet press to form pharmaceutically acceptable tablets.

The tablets were monitored for weight, hardness, thickness and friability. The tablets were tested for assay, release characteristics (in-vitro dissolution method) and abuse deterrent properties.

Samples of the tablets were subjected to dissolution testing using USP Apparatus 2 (U.S. Pharmacopoeia, XXVI, 2003), speed 50 rpm at 37° C., in purified water as dissolution medium for a period of 90 minutes. The acceptable dissolution criterion is not less than 75 percent of the drug dissolved in 45 minutes.

To evaluate abuse deterrent properties of the formulation a method has been developed that mimics the street abuser's method for abuse.

(i) The tablets are crushed and the resulting powder is placed into table/teaspoon.
(ii) Measured amount of water is added to the spoon. Contents of the spoon are heated for about 1 to 2 minutes.
(iii) Contents of the spoon are withdrawn using a syringe equipped with a needle.
(iv) The volume of the sample removed from the spoon is measured and the contents of the syringe are tested for the active, using a suitable analytical test method such as UV/VIS spectrophotometry.

TABLE 1

| Component | Weight (mg)/tablet |
| --- | --- |
| Hydrocodone bitartrate | 5 |
| Polyvinyl alcohol | 160 |
| Avicel PH 102 | 333 |
| Starch 21 | 54 |
| Zinc sulfate | 30 |
| Explotab | 15 |
| Cab-O-Sil | 1.5 |
| Magnesium stearate | 1.5 |
| Total | 600 |

An in-vitro dissolution criterion of NLT 75% of the drug dissolved in 45 minutes was met.

The drug extracted by the abuse-test method detailed above was about 34 percent.

Example 2

TABLE 2

| Component | Weight (mg)/tablet |
| --- | --- |
| Hydrocodone bitartrate | 5 |
| Polyvinyl alcohol | 160 |
| Crospovidone | 90 |
| Avicel PH 102 | 120 |
| Starch 21 | 43 |
| Zinc sulfate | 30 |
| Cab-O-Sil | 1 |
| Magnesium stearate | 1 |
| Total | 450 |

As shown by Table 2, a direct compression formulation of hydrocodone bitartrate immediate release formulation including a dosage of 5 mg of hydrocodone bitartrate was prepared and tested using the blending conditions and procedure as stated in Example 1.

An in-vitro dissolution criterion of NLT 75% of the drug dissolved in 45 minutes was met.

The drug extracted by the abuse-test method was about 31 percent.

Example 3

TABLE 3

| Component | Weight (mg)/tablet |
|---|---|
| Hydrocodone bitartrate | 5 |
| Polyox | 70 |
| Crospovidone | 152 |
| Avicel PH 102 | 304 |
| Zinc sulfate | 150 |
| Sodium lauryl sulfate | 1 |
| Cab-O-Sil | 14 |
| Magnesium stearate | 4 |
| Total | 700 |

As shown by Table 3, a direct compression formulation of hydrocodone bitartrate immediate release formulation including a dosage of 5 mg of hydrocodone bitartrate was prepared and tested using the blending conditions and procedure as stated in Example 1.

An in-vitro dissolution criterion of NLT 75% of the drug dissolved in 45 minutes was met.

The drug extracted by the abuse-test method was about 11 percent.

Example 4

TABLE 4

| Component | Weight (mg)/tablet |
|---|---|
| Hydrocodone bitartrate | 5 |
| Polyvinyl alcohol | 80 |
| Polyox | 15 |
| Avicel PH 102 | 300 |
| Zinc sulfate | 50 |
| Sodium lauryl sulfate | 7 |
| Crospovidone | 100 |
| Cab-O-Sil | 2 |
| Magnesium stearate | 1 |
| Total | 560 |

As shown by Table 4, a direct compression formulation of hydrocodone bitartrate immediate release formulation including a dosage of 5 mg of hydrocodone bitartrate was prepared and tested using the blending conditions and procedure as stated in Example 1.

An in-vitro dissolution criterion of NLT 75% of the drug dissolved in 45 minutes was met.

The drug extracted by the abuse-test method was about 6.5 percent.

Example 5

TABLE 5

| Component | Weight (mg)/tablet |
|---|---|
| Hydrocodone bitartrate | 5 |
| Methocel K100 LV | 25 |
| Avicel PH 102 | 300 |
| Zinc sulfate | 50 |
| Sodium lauryl sulfate | 7 |
| Crospovidone | 100 |
| Cab-O-Sil | 2 |
| Magnesium stearate | 1 |
| Total | 490 |

As shown by Table 5, a direct compression formulation of hydrocodone bitartrate immediate release formulation including a dosage of 5 mg of hydrocodone bitartrate was prepared and tested using the blending conditions and procedure as stated in Example 1.

An in-vitro dissolution criterion of NLT 75% of the drug dissolved in 45 minutes was met.

The drug extracted by the abuse-test method was about 17 percent.

Example 6

TABLE 6

| Component | Weight (mg)/tablet |
|---|---|
| Oxycodone hydrochloride | 5 |
| Polyox | 25 |
| Avicel PH 102 | 300 |
| Zinc sulfate | 50 |
| Sodium lauryl sulfate | 7 |
| Crospovidone | 100 |
| Cab-O-Sil | 2 |
| Magnesium stearate | 1 |
| Total | 490 |

As shown by Table 6, a direct compression formulation of oxycodone hydrochloride immediate release formulation including a dosage of 5 mg of oxycodone hydrochloride was prepared and tested using the blending conditions and procedure as stated in Example 1.

An in-vitro dissolution criterion of NLT 70% of the drug dissolved in 45 minutes was met.

The drug extracted by the abuse-test method was about 9 percent.

Example 7

TABLE 7

| Component | Weight (mg)/tablet |
|---|---|
| Morphine sulfate | 20 |
| Polyox | 20 |
| Avicel PH 102 | 300 |
| Zinc sulfate | 50 |
| Sodium lauryl sulfate | 7 |
| Crospovidone | 100 |

TABLE 7-continued

| Component | Weight (mg)/tablet |
| --- | --- |
| Cab-O-Sil | 2 |
| Magnesium stearate | 1 |
| Total | 500 |

As shown by Table 7, a direct compression formulation of morphine sulfate immediate release formulation including a dosage of 20 mg of morphine sulfate was prepared and tested using the blending conditions and procedure as stated in Example 1.

An in-vitro dissolution criterion of NLT 75% of the drug dissolved in 45 minutes was met.

The drug extracted by the abuse-test method was about 16 percent.

Example 8

TABLE 8

| Component | Weight (mg)/tablet |
| --- | --- |
| Morphine sulfate | 20 |
| Polyvinyl alcohol | 160 |
| Avicel PH 102 | 318 |
| Zinc sulfate | 30 |
| Explotab | 30 |
| Starch 21 | 54 |
| Cab-O-Sil | 1.5 |
| Magnesium stearate | 1.5 |
| Total | 615 |

As shown by Table 8, a direct compression formulation of morphine sulfate immediate release formulation including a dosage of 20 mg of morphine sulfate was prepared and tested using the blending conditions and procedure as stated in Example 1.

An in-vitro dissolution criterion of NLT 75% of the drug dissolved in 45 minutes was met.

The drug extracted by the abuse-test method was about 12 percent.

Example 9

TABLE 9

| Component | Weight (mg)/tablet |
| --- | --- |
| Morphine sulfate | 40 |
| Polyox | 15 |
| Avicel PH 102 | 300 |
| Zinc sulfate | 50 |
| Sodium lauryl sulfate | 7 |
| Crospovidone | 100 |
| Cab-O-Sil | 2 |
| Magnesium stearate | 1 |
| Total | 515 |

As shown by Table 9, a direct compression formulation of morphine sulfate immediate release formulation including a dosage of 40 mg of morphine sulfate was prepared and tested using the blending conditions and procedure as stated in Example 1.

An in-vitro dissolution criterion of NLT 75% of the drug dissolved in 45 minutes was met.

The drug extracted by the abuse-test method was about 15 percent.

Example 10

TABLE 10

| Component | Weight (mg)/tablet |
| --- | --- |
| Morphine sulfate | 40 |
| Polyvinyl alcohol | 200 |
| Avicel PH 102 | 278 |
| Zinc sulfate | 30 |
| Explotab | 30 |
| Starch 21 | 54 |
| Cab-O-Sil | 1.5 |
| Magnesium stearate | 1.5 |
| Total | 635 |

As shown by Table 10, a direct compression formulation of morphine sulfate immediate release formulation including a dosage of 40 mg of morphine sulfate was prepared and tested using the blending conditions and procedure as stated in Example 1.

An in-vitro dissolution criterion of NLT 75% of the drug dissolved in 45 minutes was met.

The drug extracted by the abuse-test method was about 6 percent.

Example 11

TABLE 11

| Component | Weight (mg)/tablet |
| --- | --- |
| Hydrocodone bitartrate | 7.5 |
| Polyox | 25 |
| Avicel PH 102 | 297.5 |
| Crospovidone | 100 |
| Zinc sulfate | 50 |
| Sodium lauryl sulfate | 7 |
| Cab-O-Sil | 2 |
| Magnesium stearate | 1 |
| Total | 490 |

As shown by Table 11, a direct compression formulation of hydrocodone bitartrate immediate release formulation including a dosage of 7.5 mg of hydrocodone bitartrate was prepared and tested using the blending conditions and procedure as stated in Example 1.

An in-vitro dissolution criterion of NLT 75% of the drug dissolved in 45 minutes was met.

The drug extracted by the abuse-test method was about 5 percent.

Example 12

TABLE 12

| Component | Weight (mg)/tablet |
| --- | --- |
| Hydrocodone bitartrate | 10 |
| Polyvinyl alcohol | 80 |
| Polyox | 15 |
| Avicel PH 102 | 295 |
| Crospovidone | 100 |
| Zinc sulfate | 50 |

TABLE 12-continued

| Component | Weight (mg)/tablet |
|---|---|
| Sodium lauryl sulfate | 7 |
| Cab-O-Sil | 2 |
| Magnesium stearate | 1 |
| Total | 560 |

As shown by Table 12, a direct compression formulation of hydrocodone bitartrate immediate release formulation including a dosage of 10 mg of hydrocodone bitartrate was prepared and tested using the blending conditions and procedure as stated in Example 1.

An in-vitro dissolution criterion of NLT 75% of the drug dissolved in 45 minutes was met.

The drug extracted by the abuse-test method was about 9.5 percent.

Example 13

TABLE 13

| Component | Weight (mg)/tablet |
|---|---|
| Hydrocodone bitartrate | 5 |
| Carbopol 971P | 10 |
| Avicel PH 102 | 300 |
| Crospovidone | 100 |
| Zinc sulfate | 50 |
| Sodium lauryl sulfate | 7 |
| Cab-O-Sil | 2 |
| Magnesium stearate | 1 |
| Total | 490 |

As shown by Table 13, a direct compression formulation of hydrocodone bitartrate immediate release formulation including a dosage of 5 mg of hydrocodone bitartrate was prepared and tested using the blending conditions and procedure as stated in Example 1.

An in-vitro dissolution criterion of NLT 75% of the drug dissolved in 45 minutes was met.

The drug extracted by the abuse-test method was about 27 percent.

Example 14

TABLE 14

| Formulation A3 | |
|---|---|
| Component | Weight (mg/tablet) |
| Hydrocodone Bitartrate | 5 |
| Polyvinyl Alcohol | 160 |
| Avicel PH 102 | 318 |
| Zinc Sulfate | 30 |
| Starch 21 | 54 |
| Explotab | 30 |
| Cab-O-Sil | 1.5 |
| Magnesium Stearate | 1.5 |
| Total | 600 |

As shown by Table 14, a direct compression formulation of hydrocodone bitartrate immediate release formulation including a dosage of 5 mg of hydrocodone bitartrate was prepared and tested using the blending conditions and procedure as stated in Example 1.

An in-vitro dissolution showed about 62% of the drug dissolved in 45 minutes.

The drug extracted by the abuse-test method was about 26.77 percent.

Example 15

TABLE 15

| Formulation B3 | |
|---|---|
| Component | Weight (mg/tablet) |
| Hydrocodone Bitartrate | 5 |
| Polyvinyl Alcohol | 160 |
| Avicel PH 102 | 333 |
| Zinc Sulfate | 30 |
| Explotab | 15 |
| Starch 21 | 54 |
| Cab-O-Sil | 1.5 |
| Magnesium Stearate | 1.5 |
| Total | 600 |

As shown by Table 15, a direct compression formulation of hydrocodone bitartrate immediate release formulation including a dosage of 5 mg of hydrocodone bitartrate was prepared and tested using the blending conditions and procedure as stated in Example 1.

An in-vitro dissolution showed about 72% of the drug dissolved in 45 minutes.

The drug extracted by the abuse-test method was about 31.8 percent.

Example 16

TABLE 16

| Formulation C3 | |
|---|---|
| Component | Weight (mg/tablet) |
| Hydrocodone Bitartrate | 5 |
| Polyvinyl Alcohol | 160 |
| Avicel PH 102 | 120 |
| Zinc Sulfate | 30 |
| Crospovidone (PVP XL) | 40 |
| Starch 21 | 43 |
| Cab-O-Sil | 1 |
| Magnesium Stearate | 1 |
| Total | 400 |

As shown by Table 16, a direct compression formulation of hydrocodone bitartrate immediate release formulation including a dosage of 5 mg of hydrocodone bitartrate was prepared and tested using the blending conditions and procedure as stated in Example 1.

An in-vitro dissolution showed about 75% of the drug dissolved in 45 minutes.

The drug extracted by the abuse-test method was about 35.75 percent.

Example 17

TABLE 17

Formulation D3

| Component | Weight (mg/tablet) |
|---|---|
| Hydrocodone Bitartrate | 5 |
| Polyvinyl Alcohol | 160 |
| Avicel PH 102 | 120 |
| Zinc Sulfate | 30 |
| Crospovidone (PVP XL) | 100 |
| Starch 21 | 33 |
| Cab-O-Sil | 1 |
| Magnesium Stearate | 1 |
| Total | 450 |

As shown by Table 17, a direct compression formulation of hydrocodone bitartrate immediate release formulation including a dosage of 5 mg of hydrocodone bitartrate was prepared and tested using the blending conditions and procedure as stated in Example 1.

An in-vitro dissolution showed about 82% of the drug dissolved in 45 minutes.

The drug extracted by the abuse-test method was about 35.8 percent.

Example 18

TABLE 18

Formulation E3

| Component | Weight (mg/tablet) |
|---|---|
| Hydrocodone Bitartrate | 5 |
| Polyvinyl Alcohol | 160 |
| Avicel PH 102 | 333 |
| Zinc Sulfate | 30 |
| Starch 21 | 54 |
| Crospovidone (PVP XL) | 15 |
| Cab-O-Sil | 1.5 |
| Magnesium Stearate | 1.5 |
| Total | 600 |

As shown by Table 18, a direct compression formulation of hydrocodone bitartrate immediate release formulation including a dosage of 5 mg of hydrocodone bitartrate was prepared and tested using the blending conditions and procedure as stated in Example 1.

An in-vitro dissolution showed about 79% of the drug dissolved in 45 minutes.

The drug extracted by the abuse-test method was about 42.5 percent.

Example 19

TABLE 19

Formulation F3

| Component | Weight (mg/tablet) |
|---|---|
| Hydrocodone Bitartrate | 5 |
| Polyvinyl Alcohol | 160 |
| Avicel PH 102 | 119 |
| Zinc Sulfate | 30 |
| Crospovidone (PVP XL) | 100 |
| Starch 21 | 33 |
| Cab-O-Sil | 1 |
| Magnesium Stearate | 2 |
| Total | 450 |

As shown by Table 19, a direct compression formulation of hydrocodone bitartrate immediate release formulation including a dosage of 5 mg of hydrocodone bitartrate was prepared and tested using the blending conditions and procedure as stated in Example 1.

An in-vitro dissolution criterion of NLT 75% of the drug dissolved in 45 minutes was met.

The drug extracted by the abuse-test method was about 54 percent.

Example 20

TABLE 20

| Component | Weight (mg/tablet) |
|---|---|
| Hydrocodone Bitartrate | 5 |
| Polyvinyl Alcohol | 95 |
| Avicel PH 102 | 192 |
| Zinc Sulfate | 30 |
| Starch 21 | 140 |
| Ac-Di-Sol | 35 |
| Cab-O-Sil | 1 |
| Magnesium Stearate | 2 |
| Total | 500 |

As shown in Table 20, a direct compression formulation of hydrocodone bitartrate immediate release formulation including a dosage of 5 mg of hydrocodone bitartrate was prepared and tested using the blending conditions and procedure as stated in Example 1.

An in-vitro dissolution criterion of NLT 75% of the drug dissolved in 45 minutes was met.

The drug extracted by the abuse-test method was about 60 percent.

Example 21

TABLE 21

| Component | Weight (mg/tablet) |
|---|---|
| Oxycodone Hydrochloride | 5 |
| Avicel PH 102 | 119 |
| Zinc Sulfate | 30 |
| Crospovidone (PVP XL) | 100 |

TABLE 21-continued

| Component | Weight (mg/tablet) |
|---|---|
| Starch 21 | 33 |
| Cab-O-Sil | 1 |
| Magnesium Stearate | 2 |
| Total | 290 |

As shown by Table 21, a direct compression formulation of hydrocodone bitartrate immediate release formulation including a dosage of 5 mg of hydrocodone bitartrate was prepared and tested using the blending conditions and procedure as stated in Example 1.

An in-vitro dissolution criterion of NLT 75% of the drug dissolved in 45 minutes was met.

The drug extracted by the abuse-test method was about 94 percent.

Example 22

TABLE 22

| Component | Weight (mg/tablet) |
|---|---|
| Hydrocodone Bitartrate | 5 |
| Polyvinyl Alcohol | 50 |
| Avicel PH 102 | 192 |
| Zinc Sulfate | 30 |
| Starch 21 | 140 |
| Ac-Di-Sol | 35 |
| Cab-O-Sil | 1 |
| Magnesium Stearate | 2 |
| Total | 455 |

As shown in Table 22, a direct compression formulation of hydrocodone bitartrate immediate release formulation including a dosage of 5 mg of hydrocodone bitartrate was prepared and tested using the blending conditions and procedure as stated in Example 1.

An in-vitro dissolution criterion of NLT 75% of the drug dissolved in 45 minutes was met.

The drug extracted by the abuse-test method was about 70 percent.

Example 23

TABLE 23

| Component | Weight (mg/tablet) |
|---|---|
| Hydrocodone Bitartrate | 5 |
| Polyvinyl Alcohol | 160 |
| Avicel PH 102 | 318 |
| Zinc Sulfate | 30 |
| Explotab | 30 |
| Cab-O-Sil | 1.5 |
| Magnesium Stearate | 1.5 |
| Total | 600 |

As shown in Table 23, a direct compression formulation of hydrocodone bitartrate immediate release formulation including a dosage of 5 mg of hydrocodone bitartrate was prepared and tested using the blending conditions and procedure as stated in Example 1.

An in-vitro dissolution criterion of NLT 75% of the drug dissolved in 45 minutes was met.

The drug extracted by the abuse-test method was about 33 percent.

Example 24

TABLE 24

| Component | Weight (mg/tablet) |
|---|---|
| Hydrocodone Bitartrate | 10 |
| Avicel PH 102 | 318 |
| Zinc Sulfate | 50 |
| Crospovidone (PVP XL) | 100 |
| Sodium Lauryl Sulfate | 7 |
| Cab-O-Sil | 1.5 |
| Magnesium Stearate | 1.5 |
| Total | 488 |

As shown in Table 24, a direct compression formulation of hydrocodone bitartrate immediate release formulation including a dosage of 5 mg of hydrocodone bitartrate was prepared and tested using the blending conditions and procedure as stated in Example 1.

An in-vitro dissolution criterion of NLT 75% of the drug dissolved in 45 minutes was met.

The drug extracted by the abuse-test method was about 85 percent.

Example 25

TABLE 25

| Formulation A7 | |
|---|---|
| Component | Weight (mg/tablet) |
| Hydrocodone Bitartrate | 22 |
| Polyvinyl Alcohol | 250 |
| Cab-O-Sil | 1.38 |
| Magnesium Stearate | 2.76 |
| Total | 276.14 |

An in-vitro dissolution showed about 98% dissolution after 10 hours.

Example 26

TABLE 26

| Formulation B7 | |
|---|---|
| Component | Weight (mg/tablet) |
| Hydrocodone Bitartrate | 44 |
| Polyvinyl Alcohol | 450 |
| Cab-O-Sil | 1.5 |
| Magnesium Stearate | 2.0 |
| Total | 497.5 |

An in-vitro dissolution showed about 82% dissolution after 10 hours.

Example 27

TABLE 27

| Formulation C7 | |
|---|---|
| Component | Weight (mg/tablet) |
| Hydrocodone Bitartrate | 88 |
| Polyvinyl Alcohol | 600 |
| Cab-O-Sil | 1.5 |
| Magnesium Stearate | 2.0 |
| Total | 691.5 |

An in-vitro dissolution showed about 80% dissolution after 10 hours.

Example 28

TABLE 28

| Component | Weight (mg)/tablet |
|---|---|
| Oxycodone hydrochloride | 5 |
| Polyox | 25 |
| Avicel PH 102 | 250 |
| Zinc sulfate | 100 |
| Sodium lauryl sulfate | 7 |
| Crospovidone | 100 |
| Cab-O-Sil | 2 |
| Magnesium stearate | 1 |
| Total | 490 |

As shown by Table 28, a direct compression formulation of oxycodone hydrochloride immediate release formulation including a dosage of 5 mg of oxycodone hydrochloride was prepared using the blending conditions and procedure as stated in Example 1.

Example 29

TABLE 29

| Component | Weight (mg)/tablet |
|---|---|
| Oxycodone hydrochloride | 5 |
| Polyox | 25 |
| Avicel PH 102 | 200 |
| Zinc sulfate | 150 |
| Sodium lauryl sulfate | 7 |
| Crospovidone | 100 |
| Cab-O-Sil | 2 |
| Magnesium stearate | 1 |
| Total | 490 |

As shown by Table 29, a direct compression formulation of oxycodone hydrochloride immediate release formulation including a dosage of 5 mg of oxycodone hydrochloride was prepared using the blending conditions and procedure as stated in Example 1.

It will be appreciated by persons skilled in the art that numerous variations and/or modifications may be made to the invention shown in the specific embodiments without departing form the spirit and scope of the invention as broadly described. Further, each and every reference cited above is hereby incorporated by reference as if fully set forth herein.

What is claimed is:

1. An extended release abuse deterrent dosage form comprising:
   a. a core matrix comprising a blended mixture of:
      (a) PEO having a molecular weight of from about 300,000 to about 5,000,000;
      (b) magnesium stearate; and
      (c) oxycodone or a pharmaceutically acceptable salt thereof;
   wherein the matrix is heated to melt at least a portion of the PEO included in the matrix; and
   b. PEG applied onto the core matrix;
   wherein the dosage form provides extended release of the drug.

* * * * *